United States Patent

Fukaya et al.

Patent Number: 5,486,275
Date of Patent: Jan. 23, 1996

[54] NITROGEN-CONTAINING PERFLUOROALKYL BROMIDE AND METHOD FOR PRODUCTION THEREOF

[75] Inventors: Haruhiko Fukaya, Oobu; Takashi Abe, Kasugai; Eiji Hayashi, Konan; Yoshio Hayakawa, Aichi; Hajime Baba, Nagoya, all of Japan

[73] Assignee: Agency of Industrial Science & Technology, Ministry of International Trade & Industry, Tokyo, Japan

[21] Appl. No.: 293,963

[22] Filed: Aug. 24, 1994

Related U.S. Application Data

[62] Division of Ser. No. 22,463, Feb. 25, 1993, abandoned.

[30] Foreign Application Priority Data

Feb. 28, 1992 [JP] Japan .......................... 4-78887

[51] Int. Cl.$^6$ ............................................ C07C 2/00
[52] U.S. Cl. ................. 204/157.6; 204/157.61; 204/157.64; 204/157.71; 204/157.81; 204/157.94; 204/158.11
[58] Field of Search .................... 204/157.6, 157.61, 204/157.64, 157.71, 157.81, 157.94, 158.11

[56] References Cited

FOREIGN PATENT DOCUMENTS 05229992  9/1993  Japan .

Primary Examiner—John Niebling
Assistant Examiner—C. Delacroix-Muirheid
Attorney, Agent, or Firm—Oblon, Spivak, McClelland, Maier & Neustadt

[57] ABSTRACT

A nitrogen-containing perfluoroalkyl bromide, a novel compound to the art, is represented by the formula,

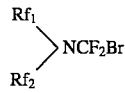

wherein $Rf_1$ and $Rf_2$ independently stand for a perfluoroalkyl group of one to five carbon atoms, provided that $Rf_1$ and $Rf_2$ are 1) separated from each other, 2) directly bonded to each other, 3) bonded to each other through the medium of an oxygen atom, or 4) bonded to each other through the medium of a nitrogen atom. This novel compound is produced by decarbonylating a nitrogen-containing perfluorocarboxylic acid bromide represented by the formula,

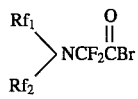

by exposure to an ultraviolet light.

12 Claims, No Drawings

NITROGEN-CONTAINING PERFLUOROALKYL BROMIDE AND METHOD FOR PRODUCTION THEREOF

This is a division of application Ser. No. 08/022,463 filed on Feb. 25, 1993, now abandoned.

BACKGROUND OF THE INVENTION

1. Field of the Invention

This invention relates to a novel nitrogen-containing perfluoroalkyl bromide and a method for the production thereof. More particularly, this invention relates to a nitrogen-containing perfluoroalkyl bromide which is useful as an intermediate for the synthesis of fluorine-containing products such as surfactants, agricultural pesticides, and medicines, as a halon type fire extinguisher gas, as a flame-retarding additive for transformer oil and electric insulating oil, and as an X-ray contrast medium, and to a method for producing this compound economically from a readily available raw material in a high yield.

2. Prior Art Statement

A perfluoroalkyl bromide has a relatively weak bond between the perfluoroalkyl group and the bromine thereof. This bond easily cleaved. It is therefore known as a compound for the introduction of a perfluoroalkyl group and is used as the raw material for the synthesis of fluorine-containing products such as surfactants, agricultural pesticides, and medicines. It is further useful by itself as a halon type fire extinguisher gas, as a flame-retarding additive for transformer oil and electric insulating oil, and as an X-ray contrast medium, for example.

Recently, since such undecomposable CFC and halon type compounds are thought to deplete the ozone layer, their use is being phased out. Efforts are therefore being devoted to the development of substitutes for these compounds. The substitutes for the sparingly decomposable halon type compounds which are now widely used in gaseous type fire extinguishers are required to decompose before reaching the stratosphere.

As decomposable, halon compounds, there have been developed hydrofluorobromocarbon (HFBC) and hydrofluorocarbon (HFC). These are produced by the introduction of hydrogen atoms into perfluoro compounds, which gives them appropriate decomposability. Further as compounds useful for the protection of the ozone layer and the prevention of global warming, the development of fluorine compounds made decomposable by the introduction of hetero atoms have also been proposed ["Introduction to Chemistry", No. 11, page 94 (1991)].

A nitrogen-containing perfluoroalkyl bromide has the various properties required of a halon compound substitute and, therefore, is expected to find acceptance as a new type fire extinguisher gas. Methods for producing specific nitrogen-containing perfluoroalkyl bromides known to the art to date include: a method which produces perfluoro(N,N-dimethyl-2-bromoethyl amine) by exposing N-bromo-bis-trifluoromethyl)amine and tetrafluoroethylene to sunlight at 25° C. for a long time ["Journal of Chemical Society", page 6,141 (1965)], a method which produces perfluoro(N,N-dimethyl-2-bromopropyl amine) by causing N-bromo-bis-(trifluoromethyl)amine to react with hexafluoropropene at 100° C. for 24 hours ["Journal of American Chemical Society", Vol. 80, page 3,604], and a method which produces a nitrogen-containing perfluoroalkyl bromide by causing a nitrogen-containing perfluorocarboxylic acid fluoride to react with lithium bromide at a temperature in the range of from 200° to 500° C. (Japanese Patent Application No. 82729/1989). The products obtained by these methods are compounds having a bromine atom bonded to the β-carbon atom of perfluoroamine.

Thus, there is a need for the development of novel nitrogen-containing perfluoroalkyl bromides with more extensive utility than the known nitrogen-containing perfluoroalkyl bromides, as intermediates for the synthesis of surfactants, agricultural pesticides, and medicines, as a halon type fire extinguisher gas, as a flame-retarding additive for transformer oil and electric insulating oil, and as an X-ray contrast medium.

SUMMARY OF THE INVENTION

The inventors conducted a study with a view to meeting this need and found that a novel nitrogen-containing perfluoroalkyl bromide, a perfluoro-tert-amine containing a bromodifluoromethyl group, can be produced in good yield by using a nitrogen-containing perfluorocarboxylic acid bromide as a raw material and subjecting this raw material to decarbonylation by exposure to the ultraviolet light. This invention was completed on the basis of this knowledge.

To be specific, this invention is directed to a nitrogen-containing perfluoroalkyl bromide represented by the formula:

wherein $Rf_1$ and $Rf_2$ independently stand for a perfluoroalkyl group of one to five carbon atoms, provided that 1) $Rf_1$ and $Rf_2$ are separated from each other,
2) $Rf_1$ and $Rf_2$ are directly bonded to each other,
3) $Rf_1$ and $Rf_2$ are bonded to each other through the medium of an oxygen atom to form a heterocycle, or
4) $Rf_1$ and $Rf_2$ are bonded to each other through the medium of a nitrogen atom to form a heterocycle and to a method for producing the aforementioned nitrogen-containing perfluoroalkyl bromide by subjecting a nitrogen-containing perfluorocarboxylic acid bromide represented by the formula:

wherein $Rf_1$ and $Rf_2$ are independently stand for a perfluoroalkyl group of one to five carbon atoms, provided that 1) $Rf_1$ and $Rf_2$ are separated from each other,
2) $Rf_1$ and $Rf_2$ are directly bonded to each other,
3) $Rf_1$ and $Rf_2$ are bonded to each other through the medium of an oxygen atom to form a heterocycle, or
4) $Rf_1$ and $Rf_2$ are bonded to each other through the medium of a nitrogen atom to form a heterocycle to decarbonylation by exposure to ultraviolet light.

DESCRIPTION OF THE PREFERRED EMBODIMENTS

The nitrogen-containing perfluoroalkyl bromide of this invention represented by the aforementioned formula (I) is a novel compound not reported to date. The symbols $Rf_1$ and $Rf_2$ used in the formula (I) independently stand for a perfluoroalkyl group of one to five carbon atoms. They may be bonded directly to each other or they may be bonded to each other through the medium of an oxygen atom or a nitrogen atom to form a five-member, six-member, or seven-member heterocycle.

Concrete examples of the substituent part,

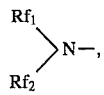

of the aforementioned formula (I) are shown below.

a) The examples having $Rf_1$ and $Rf_2$ separated from each other are represented by the following formula:

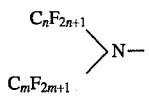

(wherein n and m independently stand for an integer in the range of from 1 to 5).

b) The examples having $Rf_1$ and $Rf_2$ directly bonded to each other as represented by the formula,

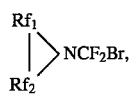

are shown below:

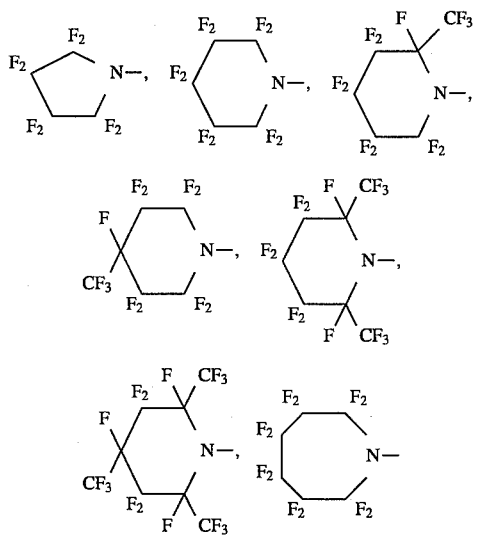

c) The examples having $Rf_1$ and $Rf_2$ bonded to each other through the medium of an oxygen atom as represented by the formula,

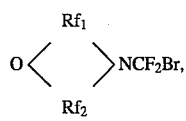

are as follows:

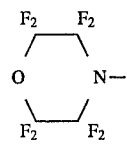

d) The examples having $Rf_1$ and $Rf_2$ bonded to each other through the medium of a nitrogen atom as represented in the formula,

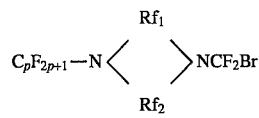

(wherein p stands for an integer in the range of from 1 to 4) are as follows.

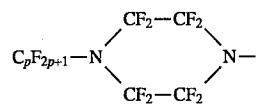

The aforementioned perfluoroalkyl bromide of this invention is produced from a perfluoro(alkylamino group-substituted acetic acid bromide) prepared by the aforementioned formula (II). The substituent part,

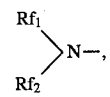

in the aforementioned formula (II) is identical with that of the formula (I).

The perfluoro(alkylamino group-substituted acetic acid bromide) can be easily obtained by electrolytically fluorinating an ester or acid halogenide of N,N-(dialkylamino) group-substituted acetic acid represented by the formula:

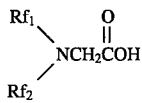 (III)

in hydrogen fluoride thereby preparing a corresponding nitrogen-containing perfluorocarboxylic acid fluoride and then subjecting the fluorination product and lithium bromide to a heat-treatment at a temperature in the range of from 230° to 270° C. The symbols $Rf_1$ and $Rf_2$ used in the formula (III) are identical to those of the formula (I).

In the method of this invention, the nitrogen-containing perfluoroalkyl bromide represented by the aforementioned formula (I) can be produced by exposing the nitrogen-containing perfluorocarboxylic acid bromide represented by the general formula (II) mentioned above to ultraviolet light. The ultraviolet light to be used for this exposure is no particularly specified beyond the sole requirement that it should possess a wavelength of not more than 400 nm. It may be suitably selected in accordance with the transmission characteristics of the substance through which the light is expected to transmit. Generally, an ultraviolet light having a wavelength in the range of from 250 to 370 nm is used for the purpose of the exposure.

The reason for this particular range is that the reaction is liable to entail a secondary reaction and produce the compound aimed at in a low yield if the wavelength is smaller than 250 nm and that the reactants show poor reactivity and the yield is low if the wavelength is greater than 370 nm.

As the light source for effecting the reaction, various kinds of commercially mercury arc lamps can be utilized. As the reaction device, reaction vessels of the inner illumination type having a light source installed as inserted into the reaction vessel are particularly appropriate. The exposure time required for completing the reaction depends on the kind of light source, the distance between the reactants and the light source, the molar ratios of reactants to light source output, the kinds of reactants, the presence or absence of dilution of the system, and the stirring condition. The end point of this reaction can be easily confirmed by analyzing (by GC and IR) the reaction mixture in the process of reaction. Though the temperature and pressure of the reaction system are not important factors for the progress of the reaction, they are desired to be such that the reaction mixture assumes a liquid phase. Generally, the reaction temperature is selected in the range of from −80° to 100° C. and the reaction pressure in the range of from 1 atmosphere to several atmospheres.

For conducting the method of this invention, it is not always necessary to use a reaction solvent. However, a reaction solvent may be used for the purpose of enhancing the effect of stirring the reaction system. No particular limitation is imposed on the amount of the reaction solvent used. If a reaction solvent is used, it is best selected with consideration to the boiling point of the product aimed at from among such fluorine type solvents as perfluoro-hexane, perfluorooctane, 1,1,2-trichlorotrifluoroethane, which are inactive and can be easily separated and refined by distilling the reaction product at the end of the reaction.

This invention allows production of a nitrogen-containing perfluoroalkyl bromide of high purity in a high yield by subjecting perfluoro(dialkylamino group-substituted acetic acid bromide), a readily procurable raw material, to decarbonylation under exposure to ultraviolet light. This product is useful as a halon substitute, namely as a fire extinguisher gas, and as an intermediate for the synthesis of fluorine-containing products.

This invention will now be described more specifically below with reference to working examples. It should be noted, however, that this invention is not limited in any respect by these examples.

EXAMPLE 1

In a quartz tube measuring 30 mm in diameter, 200 mm in length, and 2.0 mm in wall thickness, 76.8 g of perfluoro(N,N-dimethylaminoacetyl bromide) (boiling point 66° to 67° C. and purity 86.7%) was placed as a raw material under an atmosphere of argon. The upper terminal of the quartz tube was connected to a trap kept cooled to −78° C. for collection of the volatile fraction and the trailing terminal of the trap was connected to a T tube swept with nitrogen gas for protection against humidity. When the quartz tube containing the raw material was exposed for 378 hours to the ultraviolet light of 250 to 370 nm emitted from a scientific grade quartz lamp (100 W) installed at a distance of 25 mm from the quartz tube, 14.2 g of a colorless transparent liquid was obtained in the cooled trap and 57.4 g of an orange-colored liquid in the quartz tube. By GC analysis of the reaction products, it was confirmed that in proportion as the raw material perfluoro(N,N-dimethylaminoacetyl bromide) decreased, the compound of a lower boiling point than the raw material was formed as a single product. The produced compound (33.4 g) was a colorless transparent volatile compound at normal room temperature. By $^{19}$F-NMR, IR, and MS, this compound was identified to be perfluoro(N,N-dimethylaminomethyl bromide). The yield of this product based on the amount of the charged raw material perfluoro(N,N-dimethylaminoacetyl bromide) was found to be 91.9%. It was novel compound. By determination of vapor pressure using an isoteniscope, the boiling point of this compound was found to be 40.6° C. (extrapolated value). The infrared spectral data, the nuclear-magnetic resonance spectral data, and the mass analysis data of the compound were as shown below.

IR data (cm$^{-1}$): 1399 to 1414 (w), 1354 (rs), 1324 (vs), 1271 (ms), 1219 (s), 1170 (ms), 1061 (s), 1016 (w), 997 (s), 861 (s), 766 (ms), 742 (ms), 664 (w), 634 (w), 554 (w).

$^{19}$F-NMR data:

Chemical shift of $$(CF_3)_2NCF_2Br$$
$$\quad\;\; ① \quad\;\; ②$$

① - 55.0 ppm (triplet)
② - 28.2 (heptet)
Coupling constant (Hz)
① - ② = 13.6
Mass analysis data

| m/e | |
|---|---|
| 202 | [M − Br]$^+$ |
| 129 and 131 | CF$_2$Br$^+$ |
| 114 | C$_2$F$_4$N$^+$ |
| 69 | CF$_3^+$ |

EXAMPLE 2

An experiment was carried out by substantially repeating the procedure of Example 1, except that perfluoro(morpholinoacetyl bromide) was used as a raw material and the reaction was carried out in an inner radiation type photochemical reaction vessel. To be specific, the photoreaction vessel (200 ml), which was equipped with an internal insertion type high-pressure mercury lamp (400 W), was charged with 246.5 g of perfluoro(morpholinoacetyl bromide) (purity 89.9% and boiling point 105° C./490 mmHg) under an atmosphere of argon. This reaction vessel was cooled externally with cold water. The upper terminal of the quartz tube was connected to a trap kept cooled at −78° C. for collection of the volatile fraction and the trailing terminal of this trap was connected to a T tube swept with nitrogen gas for protection against humidity. When the raw material in the reaction vessel was exposed for 168 hours to an ultraviolet light of 250 to 370 nm, 216.8 g of an orange-colored liquid was obtained in the reaction vessel and 9.5 g of a colorless transparent liquid that fumed in air was obtained in the cooled trap. By GC, $^{19}$F-NMR, and MS analysis of these reaction products, the reaction was confirmed to have produced 201.9 g of perfluoro(morpholinomethyl bromide). The yield of this product based on the charged perfluoro(morpholinoacetyl bromide) was practically quantitative. This compound was a novel substance to the art. It assumed a clear liquid state at normal room temperature and possessed a boiling point of 77.0° to 78.5° C. and such physicochemical properties as $n_D^{20}$ of 1.3197 and $d_4^{20}$ of 1.9413. The infrared absorption spectral data, the nuclear-magnetic resonance spectral data, and the mass analysis data of this compound were as shown below.

IR data (cm$^{-1}$): 1409 (w), 1339 (ms), 1304 (s), 1230 (vs), 1182 (s), 1160 (s), 1132 (w), 1102 (w), 1087 (w), 1016 (m), 1000 (m), 936 (ms), 817 (w), 790 (ms), 660 (w), 626 (w)

$^{19}$F-NMR data:

| Chemical shift of | |
|---|---|
| ①②<br>F₂ F₂<br>/ \<br>O   NCF₂Br ③<br>\ /<br>F₂ F₂ | |
| ① − 85.5 ppm (singlet) | |
| ② − 92.7 (triplet) | |
| ③ − 25.9 (pentet) | |
| Coupling constant (Hz) | |
| ② − ③ = 16.1 | |
| Mass analysis data | |
| m/e | |
| 340 and 342 | $[M-F]^+$ |
| 280 | $[M-Br]^+$ |
| 164 | $C_3H_6N^+$ |
| 129 and 131 | $CF_2Br^+$ |
| 119 | $C_2F_5^+$ |
| 114 | $C_2F_4N^+$ |
| 100 | $C_2F_4^+$ |
| 69 | $CF_3^+$ |

What is claimed is:

1. A method for producing a nitrogen-containing perfluoroalkyl bromide, comprising the step of:

decarbonylating, by exposure to ultraviolet light, a nitrogen-containing perfluorocarboxylic acid bromide represented by the formula:

$$\begin{array}{c} Rf_1 \quad O \\ \phantom{Rf_1} \diagdown \parallel \\ \phantom{Rf_1 O} NCF_2CBr \\ \phantom{Rf_1} \diagup \\ Rf_2 \end{array} \quad (II)$$

wherein $Rf_1$ and $Rf_2$ independently stand for a perfluoroalkyl group of one to five carbon atoms, provided that
   1) $Rf_1$ and $Rf_2$ are separated from each other,
   2) $Rf_1$ and $Rf_2$ are directly bonded to each other,
   3) $Rf_1$ and $Rf_2$ are bonded to each other through the medium of an oxygen atom to form a heterocycle, or
   4) $Rf_1$ and $Rf_2$ are bonded to each other through the medium of a nitrogen atom to form a heterocycle.

2. A method according to claim 1, wherein $Rf_1$ and $Rf_2$ are separated from each other.

3. A method according to claim 2, wherein $Rf_1$ stands for $C_nF_{2n+1}$ wherein n is an integer in the range of 1 to 5 and $Rf_2$ for $C_mF_{2m+1}$ wherein m is an integer in the range of 1 to 5.

4. A method according to claim 1, wherein $Rf_1$ and $Rf_2$ are directly bonded to each other as shown in the formula:

$$\begin{array}{c} Rf_1 \\ | \diagdown \\ \phantom{Rf_1|} NCF_2Br. \\ | \diagup \\ Rf_2 \end{array}$$

5. A method according to claim 4, wherein the substituent part, $$\begin{array}{c} Rf_1 \\ | \diagdown \\ \phantom{Rf_1|} N-, \\ | \diagup \\ Rf_2 \end{array}$$

is at least one member selected from among the following substituents:

[ring structures shown]

6. A method according to claim 1, wherein $Rf_1$ and $Rf_2$ are bonded to each other through the medium of an oxygen atom as shown in the formula:

$$\begin{array}{c} Rf_1 \\ O \diagdown \\ \phantom{O} \diagup NCF_2Br. \\ Rf_2 \end{array}$$

7. A method according to claim 6, wherein the substituent part, $$\begin{array}{c} Rf_1 \\ O \diagdown \\ \phantom{O} \diagup N-, \\ Rf_2 \end{array}$$

is at least one member selected from among the following substituents:

$$\begin{array}{c} F_2 \quad F_2 \\ / \quad \backslash \\ O \quad\quad N-. \\ \backslash \quad / \\ F_2 \quad F_2 \end{array}$$

8. A method according to claim 1, wherein $Rf_1$ and $Rf_2$ are bonded to each other through the medium of a nitrogen atom as shown by the formula, $$C_pF_{2p+1}-N \diagup^{Rf_1}_{Rf_2} \diagdown NCF_2Br$$

wherein p stands for 1 to 4.

9. A method according to claim 8, wherein the substituent part, $$C_pF_{2p+1}-N \diagup^{Rf_1}_{Rf_2} \diagdown N- \text{ is } -N \diagup^{CF_2-CF_2}_{CF_2-CF_2} \diagdown N-.$$

10. A method according to claim 1, wherein the ultraviolet light used for the exposure has a wavelength in the range of from 250 to 370 nm.

11. A method according to claim 1, wherein said reaction of decarbonylation proceeds while the reactant is kept in a liquid state.

12. A method according to claim 11, wherein the reaction temperature is in the range of from −80° to 100° C.

* * * * *